United States Patent [19]

Marteau D'Autry

[11] Patent Number: 4,766,082
[45] Date of Patent: Aug. 23, 1988

[54] METHOD AND APPARATUS FOR PREPARING SAMPLES FOR ANALYSIS

[76] Inventor: Eric Marteau D'Autry, 1 rue Boutarel, 75004 Paris, France

[21] Appl. No.: 90,412

[22] Filed: Aug. 26, 1987

Related U.S. Application Data

[63] Continuation of Ser. No. 790,422, Oct. 23, 1985, abandoned.

[30] Foreign Application Priority Data

Oct. 24, 1984 [FR] France .................. 84 16283

[51] Int. Cl.$^4$ .................. G01N 1/18; G01N 35/02
[52] U.S. Cl. .................. 436/178; 436/47; 436/161; 422/59; 422/65; 422/70; 422/101; 210/198.2; 210/287; 73/863.32
[58] Field of Search .................. 436/47, 161, 178; 422/59, 65, 70, 101; 210/198.2, 287; 73/863.32

[56] References Cited

U.S. PATENT DOCUMENTS

| | | | |
|---|---|---|---|
| 3,443,439 | 5/1969 | Cruz | 73/863.32 |
| 3,536,452 | 10/1970 | Norton et al. | 422/63 |
| 4,155,711 | 5/1979 | Zelagin et al. | 422/65 X |
| 4,219,530 | 8/1980 | Kopp et al. | 422/101 X |
| 4,221,568 | 9/1980 | Boettger | 422/64 X |
| 4,234,317 | 11/1980 | Lucas et al. | 422/101 X |
| 4,338,280 | 7/1982 | Ambers et al. | 422/81 X |
| 4,497,711 | 2/1985 | Shepherd | 210/198.2 X |
| 4,499,053 | 2/1985 | Jones | 422/68 |

Primary Examiner—Barry S. Richman
Assistant Examiner—Lynn M. Kummert
Attorney, Agent, or Firm—Mason, Kolehmainen, Rathburn & Wyss

[57] ABSTRACT

The present invention relates to a method of preparing samples for the purpose of analysis, in which at least one reaction agent and an initial sample are successively injected into a cartridge (90) provided with an orifice (92) in its lower portion, in such a manner as to cause the injected matter to pass through a column (91) of powdery agent contained within the cartridge, and in which the product of the last passage of injected matter through the column is retained for analysis. According to the invention, the reaction agents and the initial sample are successively injected into each cartridge after the top of the cartridge has been sealed in such a manner that the injection of the reaction agent or the sample causes the pressure at the top of the cartridge to rise, thereby accelerating the passage of the reaction agent or the sample through the column. The invention also provides apparatus for performing the method, which apparatus includes a moving carriage (120) enabling a waste receptacle (130) or individual tubes (150) to be placed beneath the lower orifices of the cartridges.

6 Claims, 4 Drawing Sheets

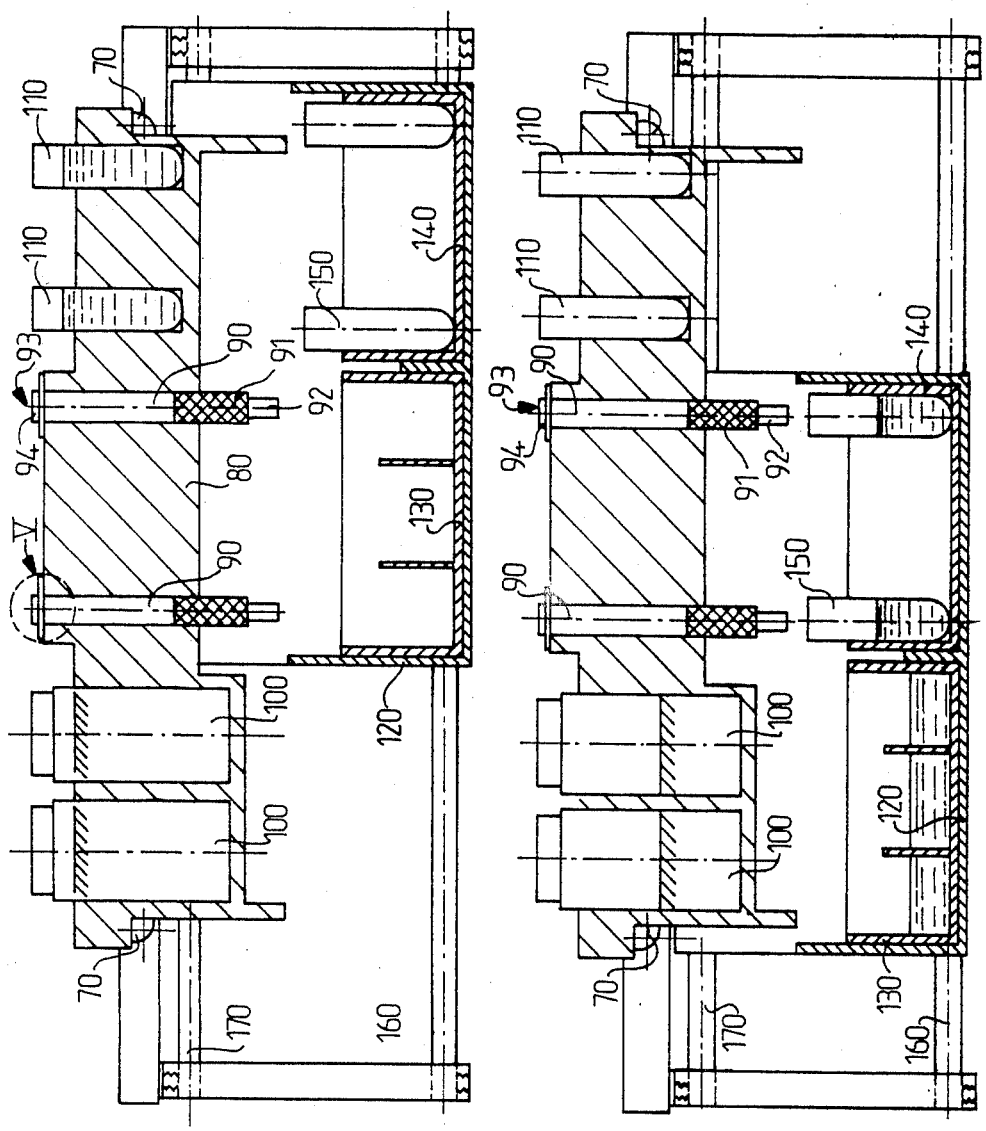
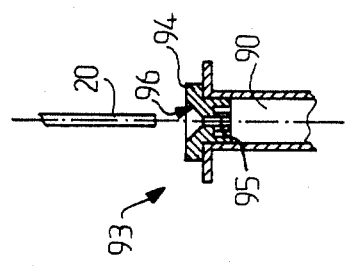
FIG-3
FIG-5
FIG-4

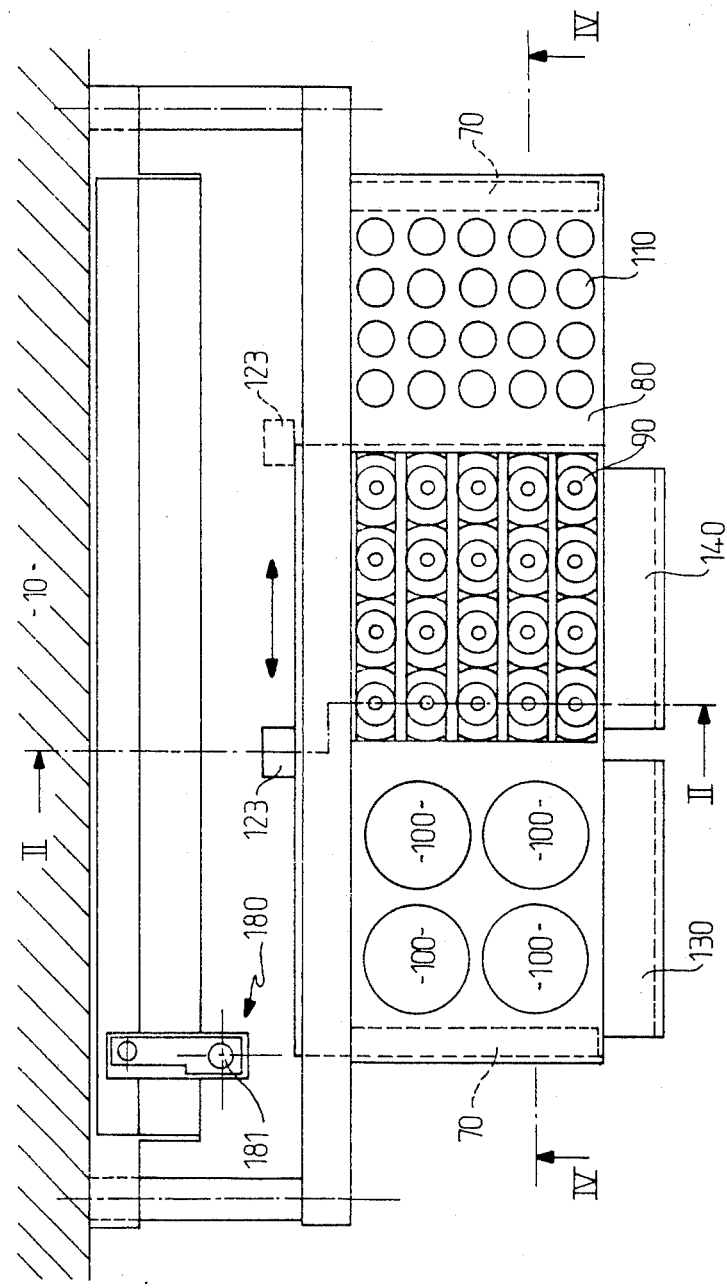

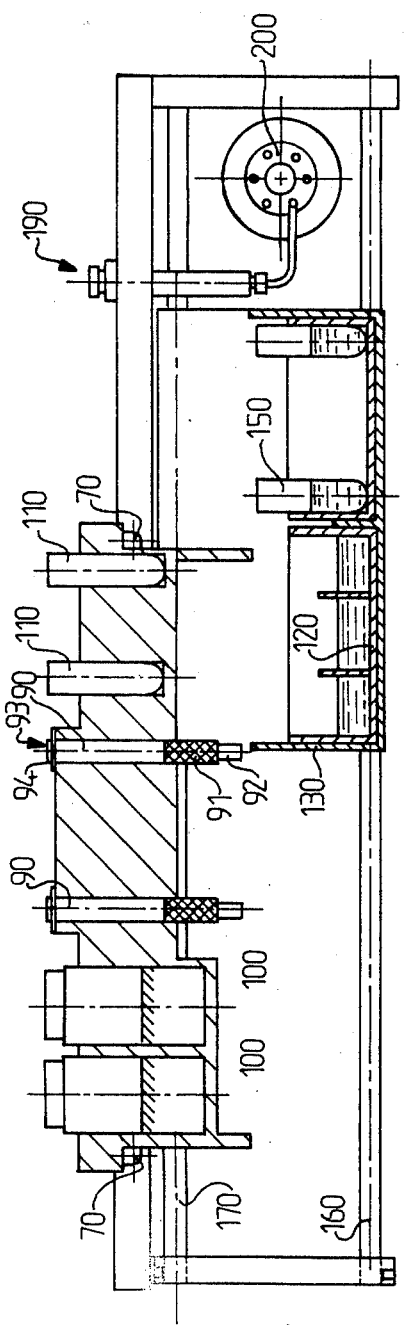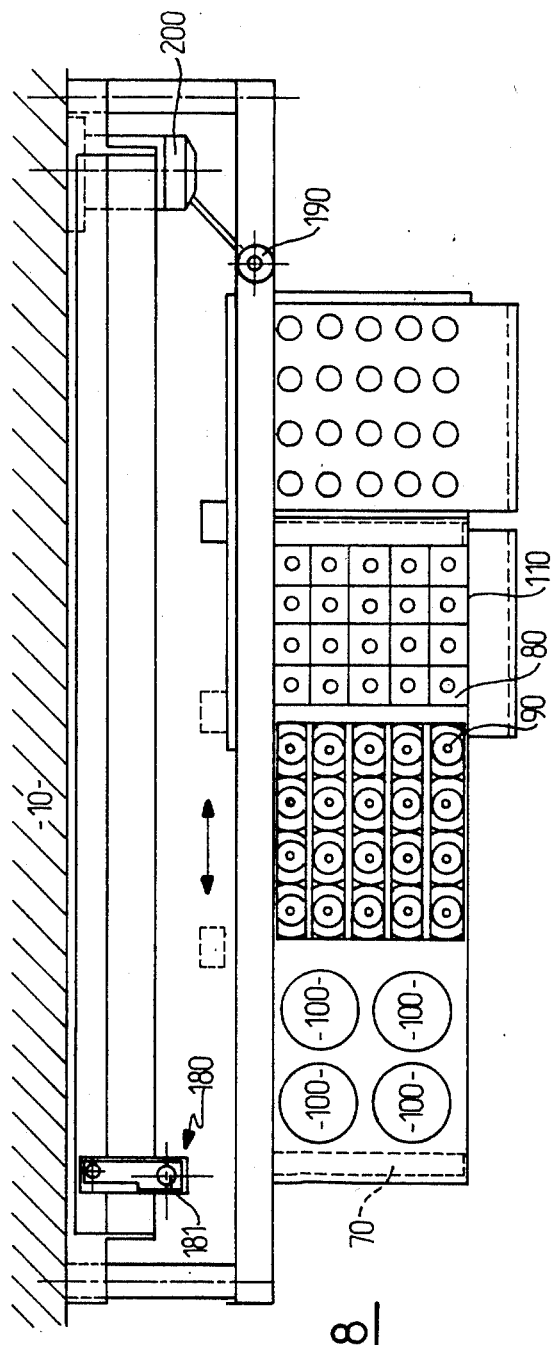

METHOD AND APPARATUS FOR PREPARING SAMPLES FOR ANALYSIS

This application is a continuation of Ser. No. 790,442, filed Oct. 23, 1985, now abandoned.

The present invention relates to a method and to apparatus for preparing samples to be analyzed.

BACKGROUND OF THE INVENTION

The invention relates to a method of preparing samples in which at least one reaction agent and an initial sample are successively injected into a cartridge containing a column of powdery agent in such a manner as to cause the injected matter to pass through the column. The cartridge also has a bottom outlet orifice, and the product of the last passage through the column is collected separately and constitutes the final sample for analysis.

The reaction agents may be injected before or after the initial sample is injected. When injected before, the reaction agents serve to impregnate the column prior to the sample being injected; when injected after, they react with a column which has already been impregnated with the sample (and optionally, with other reaction agents).

The products of most of the passages through the cartridge are rejected: only the product of one specific passages is collected for analysis purposes. If the cartridges are reusable, the last material injected may be a cleaning or reconditioning agent.

One of the drawbacks of such a method lies in the time required for the sample and the reaction agents to pass through the column which they are to impregnate.

In order to accelerate such passages, suction means are generally connected in sealed manner to the bottom outlet orifices of the cartridges. The reduced pressure set up in this manner increases the speed at which injected material passes through the column and thus reduces the total time required for preparing a sample to be analyzed.

However, such suction means are bulky devices which need to match the size of the cartridges used and which need to be used in conjunction with a vacuum pump.

Preferred implementations of the present invention provide a method which reduces the total time required for preparing samples for analysis, and which avoids the need for suction means; the apparatus is thus simplified and does not require an additional source of energy such as required by a vacuum pump, and it is easily adapted to sample-preparing apparatus already in existence.

SUMMARY OF THE INVENTION

To this end, in accordance with the invention, the reaction agents and the initial sample are successively injected into a cartridge whose top has previously been closed in sealed manner so that injecting the reaction agent or the sample causes a pressure increase at the top of the cartridge suitable for accelerating the passage of the reaction agent or the sample through the column.

Preferably, immediately after injecting the reaction agent or the sample, additional air is also injected so as to increase the previously established excess pressure.

The invention also provides apparatus for performing the method.

This apparatus is of conventional type, sometimes known as an "automatic sample preparer", i.e. it is an apparatus of the type comprising:

first support means for at least one reaction agent receptacle, for a plurality of initial samples, and for a plurality of cartridges; and a sampling and injection needle movable over the first support means and suitable for sucking predetermined quantities of a given reaction agent or of a given initial sample, and for ejecting the sucked quantity into a predetermined cartridge.

According to the invention, the apparatus further comprises:

means providing sealed co-operation between each cartridge and the needle, for closing the top of each cartridge in sealed manner after the needle has penetrated therein; and second support means located beneath the first support means, and suitable for supporting tubes or recesses disposed beneath the bottom outlet orifices the cartridges, said tubes or recesses being suitable for individually collecting for subsequent analysis the products of the final passes of injected material through respective columns.

Advantageously, the second support means are selectively movable as a function of the steps of the method between a first position and a second position in such a manner that:

in the first position a waste collector receptacle carried by the second support means is placed beneath the cartridges to recover the products of passage through the cartridges during at least one early step of the method; and in the second position individual tubes carried by the second support means are placed beneath the respective cartridges to recover the products of the final step passing through the cartridges.

Advantageously, the second support means are provided with a control lug, and the moving needle engages said control lug in such a manner as to drive said second support means and to cause them to pass from one of said positions to the other position.

Changing position is thus easily performed by an additional movement of the needle without requiring special drive means to be provided for the second support means. However, other drive means for the second support means could be provided (e.g. an independent motor of any suitable type).

BRIEF DESCRIPTION OF THE DRAWINGS

An embodiment of the invention is described by way of example with reference to the accompanying drawings, in which:

FIGS. 3 and 4 are front views of the apparatus on a section line IV—IV of FIG. 6, showing the apparatus respectively during the preliminary steps and during the final step of the method;

FIG. 5 shows a detail marked B of FIG. 3 and illustrates the structure of the top of a cartridge; and FIG. 6 is a plan view of the apparatus.

FIGS. 7 and 8 are views similar to the views of FIGS. 3 and 6, corresponding to an embodiment of the apparatus, in which the second support means may be set to a third position where the samples in the tubes can be drawn for analysis.

MORE DETAILED DESCRIPTION

Figure 1:
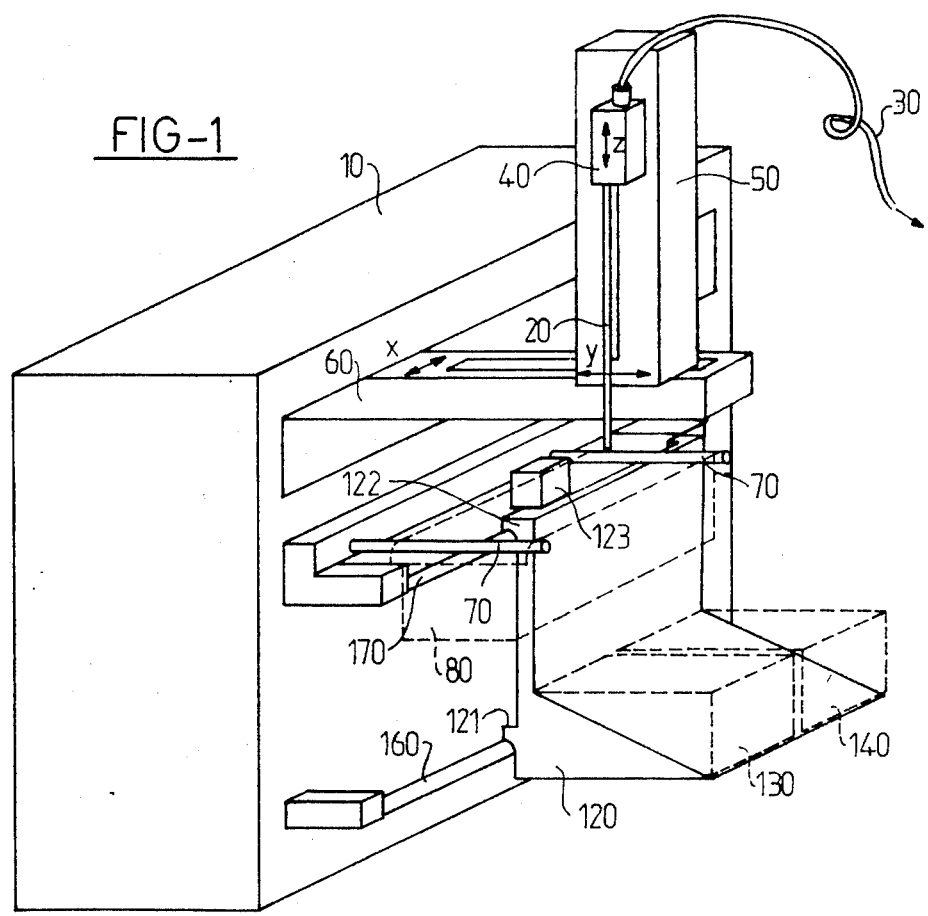
FIG. 1 is a perspective view of an apparatus in accordance with the invention.
Figure 2:
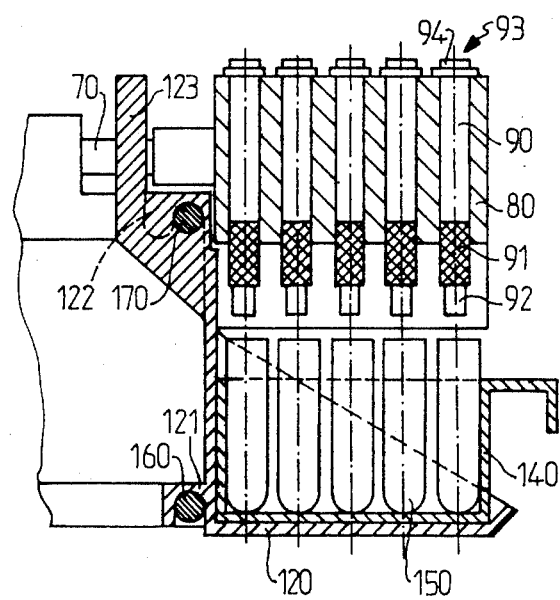
FIG. 2 is a cross-section through said apparatus on a line II—II of FIG. 6.

In the figures, reference 10 designates an automatic sample preparing apparatus of known type, for example a GILSON model "221" or "222" machine. This apparatus includes an injector needle 20 connected by a duct 30 to a suction device such as a GILSON "401" type diluter.

The needle 20 is movable along three directions X, Y, and Z under the control of moving arms 40, 50, and 60. X-Y displacement serves to place the needle over a series of tubes or receptacles capable of being selected automatically. Z displacement serves to insert the needle into the selected tube or receptacle in order to suck liquid therefrom or to inject liquid thereto, with the needle then being raised prior to displacement to some other position.

The various tubes or reaction agents (visible in the plan of FIG. 6) are supported on horizontal bars 70 which receive a support 80 which is fitted with housings for the various tubes or reaction agents.

When performing the method of the invention, the support 80 houses cartridges 90, receptacles for reaction agents 100, and as many tubes containing initial samples 100 as there are cartridges.

More precisely, the cartridges 90 (which are of a type known per se) contain a column 91 of powdery agent (a silicate for example) which is impregnated by the reaction agents and the sample as successively injected during the various steps of the method. Excess injected material (i.e. that portion of the injected material which does not react with the powdery agent) flows away via an orifice 92 at the bottom of the column.

In accordance with the invention, a closing stopper 94 (see FIG. 5) is provided at the top 93 of each tube and includes an axial orifice 95 for receiving the injection needle 90 when the needle is lowered over the center of the column for injecting a reaction agent or a sample (the funnel shape 96 serves to guide the needle as it moves downwardly).

The size of the axial orifice 95 and the resilience of the stopper 94 are chosen in such a manner that when the needle has moved fully through the stopper, the top of the cartridge is hermetically sealed.

In a variant, instead of providing each cartridge with an individual stopper, the bottom of the needle could be provided with a single common stopper which would remain fixed thereto. Sealing would then be provided when the needle is lowered over a cartridge by the stopper being pressed against the top face of the cartridge.

Also in accordance with the invention, the automatic sample preparer is provided with a carriage 120 placed beneath the support 80.

The carriage has two compartments 130 and 140, the compartment 130 is used to collect the products which have passed through the columns and which are not retained; the other compartment 140 serves to support as many individual tubes 150 as there are cartridges 90 and initial samples 110, and these tubes are used to collect the products which pass through each of the cartridges during the last step of the method.

The carriage is movable in order to allow either of the two compartments 130 and 140 to be placed beneath the cartridges 90. To this end, the automatic preparer 10 further includes two horizontal and longitudinally extending slides 160 and 170 which receive grooves 121 and 122 of complementary shape in the carriage 120. The carriage is thus free to slide on the slides 160 and 170 with one degree of freedom in the longitudinal direction.

In order to slide the carriage along the slides, an operating lug 123 projects upwardly from the carriage 120 and is offset towards the housing of the sample preparer 10.

This operating lug is situated inside the zone of possible X-Y displacement of the needle 20. Thus, in order to move the carriage, the needle is moved (automatically under the control of the sample preparer) until it comes into contact with one of the side faces of the operating lug, e.g. with the left face to move the carriage to the right or vice versa. The needle is always moved longitudinally (and automatically) in the X direction when being used to drive the moving carriage.

The operation of the apparatus is now described, as are the various steps in performing the method of the invention.

By way of example, consider a method comprising the following steps:
  impregnate the column with a reaction agent A;
  add a reaction agent B;
  add an initial sample;
  add a reaction agent C;
  add a reaction agent D.

During the first four steps the products which have passed through the cartridge are not conserved, they are simply collected prior to being discarded; however, during the last step the product of the passage through the cartridge is collected to constitute a final sample ready for analysis.

It should be assumed that the needle is washed between the various steps in order to avoid contamination. This operation may take place in conventional manner at a washing position 180 (FIG. 6) provided with an orifice 181 where the needle is washed.

The initial position of the moving carriage is the position shown in FIG. 3, i.e. the waste container 130 is placed beneath the cartridges 90.

The needle is then displaced over the receptacle 100 containing the reaction agent A, and a predetermined quantity thereof is sucked up. The needle is then placed over the first cartridge, is lowered, and then the reaction agent A is injected into the cartridge.

Because of the sealed closure of the top of the cartridge, the pressure therein increases during injection due to the combined volume of residual air and injected liquid.

This increase in pressure serves to blow the liquid through the column 91 towards the outlet orifice 92.

Advantageously, after injecting the liquid and without removing the needle, additional air is injected into the cartridge to further increase the pressure of the residual volume in the top of the cartridge.

Excess reaction agent flows out through the orifice 92 and is collected in the compartment 130.

After the needle has been washed, the same procedure is repeated to inject reaction agent B, then the individual sample taken from one of the tubes 110, and then reaction agent C.

Once the initial steps of preparing the cartridge have been completed, the moving carriage 120 is moved to the left (as shown in FIGS. 3 and 4) so that it occupies the position shown in FIG. 4, in which there is an individual tube 150 located beneath each of the columns 90 in order to collect individual final samples for analysis.

The carriage is displaced, as mentioned above, by an additional movement of the needle so as to bring it into contact with the drive lug 123 and thus drive the carriage.

Reaction agent D can then be sucked up and injected into a cartridge; it is then possible, in the same manner as before, to accelerate the passage of the liquid through the column by injecting an additional quantity of air into the top volume of the cartridge.

The final sample is then obtained in the tube 150. It is then possible to restart the cycle and to prepare the next sample, after replacing the moving carriage in its initial position (FIG. 3).

In order to reduce the total time required for preparing a series of sample, the same reaction agent may be injected into a plurality of columns during any one of the steps. Such multiple injection (into five or ten cartridges) is then followed by multiple injection of air for flushing the liquid through the respective columns.

In the embodiment shown on FIGS. 7 and 8, the movable carriage 130 is allowed to be set to a third, extreme position, where the final samples collected in tubes 150 may be drawn by the needle, then injected into an injection port 190 and directed to an injection valve 200 of a chromatograph (e.g. high pressure liquid chromatography), or any other analyser.

I claim:

1. A method of preparing samples for analysis, in which at least one reaction agent and an initial sample are successively injected into a cartridge containing a column of powdery agent and provided with a bottom outlet orifice, with said reaction agent and said sample being injected in such a manner as to pass through the column of powdery agent, and in which the product of a last passage through the column is collected for analysis, the method wherein the improvement comprises said at least one reaction agent and the initial sample are successively injected into a top of a cartridge after the top of the cartridge has been sealed in such a manner substantially effective to cause an increase in pressure at the top of the cartridge by injection of said at least one reaction agent or of the sample resulting in the acceleration of the passage of said at least one reaction agent or the sample through the column substantially as a result of said increased pressure, whereby a requirement for either a vacuum pump or pressurized gas supply is eliminated.

2. A method according to claim 1, wherein immediately after injecting said at least one reaction agent or the sample, an additional quantity of air is injected into the cartridge in order to further increase said pressure at the top of the cartride.

3. Apparatus for preparing samples for analysis including:
   first support means for supporting at least one reaction agent receptacle, a plurality of initial samples, and a plurality of cartridges, each cartridge containing a column of powdery agent and having a bottom outlet orifice; and
   a sampling and injection needle which is movable over the first support means effective to inject predetermined quantities of given reaction agent or of given initial sample into a predetermined cartridge;
   the apparatus wherein the improvement comprises:
   means providing sealed co-operation between the cartridge and the needle, to provide sealed closure of the top of the cartridge after the needle has penetrated therein substantially effective to cause an increase in pressure at said sealed closure resulting from said injection, whereby a requirement for either a vacuum pump or pressurized gas supply is eliminated; and
   second support means located beneath the first support means for supporting tubes or recesses disposed beneath the bottom outlet orifices of the cartridges, said tubes or recesses being suitable for individually collecting for subsequent analysis the products of the final passages through the respective cartridges.

4. Apparatus according to claim 3, wherein the second support means are movable means and are selectively movable between a first position and a second position,
   in the first position the tubes or recesses carried by the second support means are placed beneath the cartridges to receive the products of passages through the cartridges during at least one early step of the method; and
   in the second position, the tubes or recesses are placed beneath respective cartridges to receive the products of passages through the cartridges during a final step of the method.

5. Apparatus according to claim 4, wherein the second support means is provided with an operating lug suitable for engaging the moving needle in abutment in such a manner as to drive and move the second support means between said first and second positions.

6. Apparatus according to claim 4, wherein the second support means are further movable to a third position where the products of passages, contained in the tubes or recesses, will be drawn by the needle for injection into an analyser.

* * * * *